(12) United States Patent
Villeneuve

(10) Patent No.: US 8,873,059 B2
(45) Date of Patent: Oct. 28, 2014

(54) METHOD FOR ASSESSING AN INTERACTION OF A SAMPLE WITH LIGHT BEAMS HAVING DIFFERENT WAVELENGTHS AND A PLURALITY OF INTENSITY MODULATING FUNCTIONS

(75) Inventor: Alain Villeneuve, Mont-Royal (CA)

(73) Assignee: Genia Photononics Inc., Laval (CA)

( * ) Notice: Subject to any disclaimer, the term of this patent is extended or adjusted under 35 U.S.C. 154(b) by 550 days.

(21) Appl. No.: 13/138,491

(22) PCT Filed: Mar. 2, 2010

(86) PCT No.: PCT/CA2010/000297
§ 371 (c)(1),
(2), (4) Date: Mar. 7, 2012

(87) PCT Pub. No.: WO2010/099606
PCT Pub. Date: Sep. 10, 2010

(65) Prior Publication Data
US 2012/0162638 A1    Jun. 28, 2012

Related U.S. Application Data

(60) Provisional application No. 61/282,323, filed on Jan. 22, 2010, provisional application No. 61/202,453, filed on Mar. 2, 2009.

(51) Int. Cl.
*G01N 21/00* (2006.01)
*G01N 21/31* (2006.01)
*G01N 21/64* (2006.01)

(52) U.S. Cl.
CPC ........ *G01N 21/31* (2013.01); *G01N 2201/0691* (2013.01); *G01N 2021/6419* (2013.01); *G01N 2021/6441* (2013.01); *G01N 21/6428* (2013.01)
USPC ............ 356/434; 356/341; 356/323; 356/447

(58) Field of Classification Search
CPC ................ G01N 2021/1757; G01J 2001/4242; G01J 2003/433; G01J 2003/4332; G01J 2003/4334; G01J 2003/4336
USPC ........... 356/73, 402, 300–334, 337, 338, 341, 356/432, 434, 445, 447, 448
See application file for complete search history.

(56) References Cited

U.S. PATENT DOCUMENTS 4,415,265 A    11/1983 Campillo et al.
4,498,774 A    2/1985 Yeung et al.
(Continued)

OTHER PUBLICATIONS

Office Action by IP Australia for Australian Patent Application 2010220775 corresponding to the present US patent application, Issued on May 9, 2014.

*Primary Examiner* — Tarifur Chowdhury
*Assistant Examiner* — Michael P Lapage

(57) ABSTRACT

A method for assessing an interaction of a sample with light beams having different wavelengths, the method comprising: generating a light beam having a wavelength and being intensity modulated according to a modulation function to create an intensity modulation in the light beam; irradiating the sample with the light beam; detecting a response light from the sample, the response light being released by the sample when the sample is irradiated with the light beam, the response light having intensity fluctuations caused by the intensity modulation; using the intensity fluctuations in the response light to identify the modulation function and associate the wavelength and the response light to each other; assessing the interaction of the sample with the light beam using the response light; stopping irradiating the sample with the light beam and performing the previous step with at least one other light beam having a different wavelength. The modulation functions provide wavelength information in the light beams by encoding the wavelengths in the light beams, the wavelength information being conveyed in the response lights to allow association of the response lights respectively with a respective wavelength.

21 Claims, 3 Drawing Sheets

(56) References Cited

U.S. PATENT DOCUMENTS

| | | |
|---|---|---|
| 5,173,749 A | 12/1992 | Tell et al. |
| 5,317,162 A | 5/1994 | Pinsky et al. |
| 5,498,875 A * | 3/1996 | Obremski et al. ......... 250/458.1 |
| 5,504,337 A | 4/1996 | Lakowicz et al. |
| 5,530,541 A | 6/1996 | Ahn et al. |
| 5,929,442 A | 7/1999 | Higashi |
| 6,028,311 A | 2/2000 | Sodickson et al. |
| 6,091,504 A | 7/2000 | Walker et al. |
| 6,356,350 B1 * | 3/2002 | Silver et al. .................. 356/437 |
| 6,747,274 B2 * | 6/2004 | Li ................................. 250/288 |
| 6,949,744 B2 | 9/2005 | Steigerwald et al. |
| 7,054,002 B1 | 5/2006 | Sevick-Muraca et al. .... 356/317 |
| 7,126,682 B2 | 10/2006 | Rowe et al. |
| 7,133,130 B2 | 11/2006 | Storz et al. |
| 7,341,189 B2 | 3/2008 | Mossberg et al. |
| 7,595,878 B2 | 9/2009 | Nelson et al. |
| 2001/0002315 A1 | 5/2001 | Schultz et al. |
| 2004/0217298 A1 | 11/2004 | Bawendi et al. |
| 2006/0237665 A1 | 10/2006 | Barney et al. |
| 2007/0009884 A1 | 1/2007 | Stoughton et al. |
| 2007/0092125 A1 * | 4/2007 | Ragsdale ....................... 382/128 |
| 2007/0215795 A1 * | 9/2007 | Kameyama et al. ....... 250/222.2 |
| 2007/0221863 A1 | 9/2007 | Zipf |
| 2008/0161697 A1 * | 7/2008 | Chance ......................... 600/473 |
| 2008/0290292 A1 * | 11/2008 | Squirrell et al. ........... 250/458.1 |
| 2008/0291444 A1 * | 11/2008 | Donaldson et al. ........... 356/317 |
| 2009/0006004 A1 * | 1/2009 | Sens et al. ....................... 702/23 |
| 2009/0033944 A1 | 2/2009 | Haisch |
| 2009/0161104 A1 | 6/2009 | Schultz et al. |
| 2009/0232442 A1 | 9/2009 | Loock et al. |

\* cited by examiner

METHOD FOR ASSESSING AN INTERACTION OF A SAMPLE WITH LIGHT BEAMS HAVING DIFFERENT WAVELENGTHS AND A PLURALITY OF INTENSITY MODULATING FUNCTIONS

The present application is a National Stage Entry of PCT Application Serial Number PCT/CA2010/000297 filed on Mar. 2, 2010, which application claims priority from U.S. Provisional Patent Application Ser. No. 61/282,323 filed on Jan. 22, 2010 and U.S. Provisional Patent Application Ser. No. 61/202,453 filed on Mar. 2, 2009.

FIELD OF THE INVENTION

The present invention relates to the general field of matter-light interaction analysis, and is particularly concerned with a method for assessing an interaction of a sample with light beams having different wavelengths and an apparatus for performing the same.

BACKGROUND

Spectroscopy is used to analyze the nature of a substance under study by measuring, for example, the optical absorbance of this substance at various wavelengths. In some applications, a light source in the form of a narrow bandwidth and wavelength variable light source is used to illuminate a substance under study, and a detector is used to measure the absorbance of the substance at many wavelengths. To get the wavelength dependency of the absorbance, the detector is typically synchronized to the light source, typically by being connected thereto, so that each absorbance measurement can be matched to a specific emitted wavelength.

This need for a connection between the detector and light source can be a problem in many applications. For example, it may be the case that the distance between the light source and the detector is relatively large. In this case, there is a need to extend a cable between the light source and the detector over a relatively large distance, and possibly over difficult terrain. Also, in some applications, the detector or the light source may be mounted to a mobile unit, such as a person or a vehicle. In these cases, the use of a cable is clearly impractical.

In other applications, a sample includes a spatial distribution of indicators that respond differently to light having different wavelengths. For examples, in cellular biology experiments, chromophores that attach to different biological structures are provided, the chromophores each reacting to a specific wavelength of light to emit light at a different wavelength, thereby allowing imaging of the spatial distribution of each chromophore. Each emitted wavelength requires its own detector that receives light that has been separated in its component wavelengths, which can result in relatively complex and expensive setups.

More generally speaking, there is a need in many fields to assess the interaction of a sample with light at different wavelengths. To that effect, light beams including each of the wavelengths are used to irradiate the sample in succession. However, transmitting the information about which wavelength is used to a detector that detects the light resulting from the interaction of the sample with each light beams can be impractical. Also, transmission of this information can cause synchronization problems and can reduce the speed at which the light beams can be switched from one to the other.

Against this background, there exists a need in the industry to provide an improved method for assessing an interaction of a sample with light beams having different wavelengths and an apparatus for performing the same. An object of the present invention is therefore to provide such a method for assessing an interaction of a sample with light beams having different wavelengths and such an apparatus for performing the same.

SUMMARY OF THE INVENTION

In a broad aspect, the invention provides a method for assessing an interaction of a sample with light beams having different wavelengths, the method comprising: generating a first light beam having a first wavelength, the first light beam being intensity modulated according to a first modulation function to create a first intensity modulation in the first light beam; irradiating the sample with the first light beam; detecting a first response light from the sample, the first response light being released by the sample when the sample is irradiated with the first light beam, the first response light having first intensity fluctuations caused by the first intensity modulation; using the first intensity fluctuations in the first response light to identify the first modulation function and associate the first wavelength and the first response light to each other; assessing the interaction of the sample with the first light beam using the first response light; stopping irradiating the sample with the first light beam; generating a second light beam having a second wavelength, the second light beam being intensity modulated according to a second modulation function to create a second intensity modulation in the second light beam; irradiating the sample with the second light beam after stopping irradiating the sample with the first light beam; detecting a second response light from the sample, the second response light being released by the sample when the sample is irradiated with the second light beam, the second response light having second intensity fluctuations caused by the second intensity modulation; using the second intensity fluctuations in the second response light to identify the second modulation function and associate the second wavelength and the second response light to each other; and assessing the interaction of the sample with the second light beam using the second response light The first and second modulation functions provide wavelength information in the first and second light beams by encoding the first and second wavelengths in the first and second light beams, the wavelength information being conveyed in the first and second response lights to allow association of the first and second response lights respectively with the first and second wavelengths.

Advantageously, wavelength information is provided in the response light, for decoding, without requiring any other physical link between a light source emitting the first and second light beams and a light detector detecting the first and second response lights. This can reduce significantly the complexity and cost of apparatuses and systems performing the proposed method.

For the purpose of this document, the term light relates to electromagnetic radiations having a wavelength such that the frequency at which the light intensity is modulated is much lower than the frequency of the electromagnetic radiation contained in light. This light includes visible light, infrared radiation, ultraviolet radiations, and terahertz radiation (radiation having a frequency of from about 0.3 THz to about 3 THz). However, methods similar to the methods described in this document can be also performed at other wavelengths.

For example, assessing the interaction of the sample with the first and second light beams includes assessing an absorption of the first and second light beams by the sample, assessing a reflection of the first and second light beams by the sample, assessing scattering of the first and second light beams by the sample, assessing a non-linear interaction between the sample and the first and second light beams, or imaging a spatial distribution of emission in the sample of the first and second response lights. In another example, the first response light is emitted by the sample at a third wavelength, the third wavelength differing from the first wavelength and assessing the interaction of the sample with the first and second light beams includes assessing the emission of the first response light at the third wavelength. However, any other suitable assessment of the interaction between light and the sample are within the scope of the present invention.

The first and second modulation functions define the manner in which the intensity of the first and second light beams is modulated as a function of time to encode the first and second wavelengths in the first and second light beams. In some embodiments of the invention, the first and second modulation functions are substantially periodic, for example by being substantially sinusoidal or including a series of pulses, among other possibilities. In some embodiments of the invention, the first and second modulation functions define respectively a first phase and a second phase, the first and second phases being associated respectively with the first and second wavelengths. Decoding of this phase information can then be performed using a lock-in amplifier, or any other suitable device.

The intensity fluctuations are caused in the response lights by the intensity modulations in the respective light beams used to create the response lights. In some embodiments of the invention, the response of the sample to the intensity modulations is substantially instantaneous and the intensity fluctuations in the response lights are substantially identical to the intensity modulation in the light beams, except for a time-independent multiplicative factor. In other embodiments, the sample show a non-instantaneous response to intensity modulation in the light beams, resulting in intensity fluctuations in the response lights that have a time dependency that differs from that of the intensity modulation in the light beams. However, using well-known techniques, the modulation functions can still be retrieved in the response light if enough information is known about the sample and/or the modulation functions. It is to be noted that in many types of sample, using a periodic intensity modulation in the light beams results in periodic intensity fluctuations in the response light having a similar period, which facilitates recovering of the light beam wavelength information in the response light.

The response light may have the same wavelength as the light contained in the light beam that has generated the response light. In other embodiments, the response light has a wavelength that differs from that of the light contained in the light beam that has generated the response light. In yet other embodiments, the response light includes many component lights having each a different component wavelength. One or more of the component lights is usable for identifying the modulation functions, and the same or different component lights are usable for assessing the interaction of the sample with each light beam.

In some embodiments of the invention, the method further comprises: generating a plurality of intermediate light beams each having a respective beam wavelength comprised between the first and second wavelengths, each of the intermediate light beams being intensity modulated according to a respective intermediate modulation function to create a respective intermediate intensity modulation in each of the intermediate light beams; successively irradiating the sample with each of the intermediate light beams; detecting intermediate response lights from the sample, the intermediate response lights being each released by the sample when the sample is irradiated with a respective one of the intermediate light beams, the respective intermediate intensity modulations causing each respective intermediate intensity fluctuations in the respective intermediate response light; using the intermediate intensity fluctuations in the intermediate response lights to identify the intermediate modulation functions and associate a respective one of the intermediate wavelengths and a respective one of the intermediate response lights to each other; and assessing the interaction of the sample with the intermediate light beams using the intermediate response lights.

For example, the intermediate modulation functions are each periodic with a respective period, and, in some specific examples, for all the intermediate light beams, the periods are a monotonous function of the intermediate wavelengths.

In some embodiments of the invention, each of the intermediate light beams has a respective intermediate beam bandwidth, the intermediate light beams having beam wavelengths separated from each other by a wavelength differential substantially equal to the intermediate beam bandwidths.

In some embodiments of the invention, identifying the first modulation function in the first response light includes fitting the intensity fluctuations in the first response light to a definable function. In other embodiments, identifying the first modulation function in the first response light includes computing a Fourier transform of the intensity fluctuations in the first response lights.

In some embodiments of the invention, generating the first light beam includes generating the first light beam with a laser light source. For example, generating the first and second light beams includes generating the first and second light beams with a common laser light source, such as a common laser light source including a wavelength tunable laser. In some specific embodiments of the invention, the common laser light source is substantially continuously tunable in wavelength between the first and second wavelengths.

In some embodiments of the invention, the proposed method further comprises acquiring an image of the sample with the first response light.

In another broad aspect, the invention provides an apparatus for assessing an interaction of a sample with light beams having different wavelengths, the apparatus comprising: a substantially monochromatic wavelength tunable light source for emitting light, the light source including a modulating element for periodically modulating at a modulation frequency an intensity of the light emitted by the light source, the modulation frequency being a predetermined function of a wavelength of the light; a light guiding element optically coupled to the light source for guiding light emitted by the light source to the sample; a light detector for receiving a response light coming from the sample when the sample is illuminated with the tunable light source; and an analyzer operatively coupled to the light detector for analyzing time-varying intensity fluctuations in the response light to determine the modulation frequency.

The light guiding element is any suitable light guiding element, such as, for example, a system of discrete optical components including any number of suitable elements selected from the set consisting of mirrors, lenses and optical fibers or any other type of optical waveguide, among other possibilities.

The light detector is any element capable of detecting the response light and conveying enough information to the analyzer for allowing analysis of the response light. For example, the light detector simply detects the intensity of the response light as a function of time. However, in other examples, the light detector is more sophisticated and includes a camera for acquiring an image of the response light emitted by the sample. In yet other examples, the light detector detects an average intensity of the response light and provides other information to the analyzer to determine the modulation frequency, but without necessarily providing exhaustive intensity values. Such a detector could use a zero-crossing technique to determine the period of the response light, for example.

The analyzer includes optical and/or electronic components allowing determination of the modulation frequency. The analyzer can be as simple as an analog electronic circuit, or as complex as a general-purpose computer provided with suitable input/output ports and suitable software.

In another broad aspect, the invention provides a method for measuring a wavelength dependent spectroscopic characteristic of a sample, the method comprising: successively generating a plurality of light beams having each a respective wavelength, each of the light beams being intensity modulated according to a respective modulation function associated with the respective wavelength to create a respective intensity modulation in the light beams; successively irradiating the sample with each of the light beams; detecting a respective response light released from the sample when the sample is irradiated with each of the light beams, each of the response lights having respective intensity fluctuations caused by the intensity modulations; identifying the modulation functions in the response lights using the intensity fluctuations in each of the response lights; associating a respective one of the wavelengths to each of the response lights, the wavelength associated with each of the response lights being the wavelength associated with the modulation function identified in each of the response lights; and assessing the spectroscopic characteristic using the response lights and the wavelengths associated with the response lights.

For example, the spectroscopic characteristic is absorbance, transmittance, or reflectance, among others. In other examples, the spectroscopic characteristic is an absorption spectrum or an emission spectrum. In yet other examples, the spectroscopic characteristic is a result of an interaction of the light beams with an auxiliary light, the method further comprising illuminating the sample with the auxiliary light. In such examples, the wavelength of the response light used to decode the wavelength information can be a function of the wavelength of the two types of lights used to irradiate the sample, for example a sum of or a difference between these wavelengths. This would be the case, for example, in Raman spectroscopy, stimulated Raman spectroscopy, Coherent anti-Stokes Raman spectroscopy and many other types of spectroscopy.

In another broad aspect, the invention provides a method for imaging a distribution of predetermined structures in a biological sample using fluorescent chromophores, the method comprising: providing at least two chromophores, each of the chromophores emitting fluorescence light at a common predetermined wavelength when irradiated with light having different irradiation wavelengths, each of the chromophores being attachable to a different one of the predetermined structures; attaching the chromophores to the predetermined structures; successively generating a plurality of light beams having each a respective one of the irradiation wavelengths, each of light beams being intensity modulated in time according to a respective modulation function associated with the respective irradiation wavelength to create a respective intensity modulation in each of the light beams; successively irradiating the biological sample with each of the light beams; detecting a respective fluorescence light emitted by the biological sample at the common predetermined wavelength in response to irradiation with each of the light beams, the respective fluorescence lights having each respective intensity fluctuations caused by the intensity modulations; acquiring a respective image of the biological sample when the biological sample emits each of the fluorescence lights; identifying the modulation functions in each of the fluorescence lights using the intensity fluctuations in each of the fluorescence lights; associating a respective one of the wavelengths to each of the fluorescence lights, the wavelength associated with each of the fluorescence lights being the wavelength associated with the modulation function identified in each of the fluorescence lights; and associating with each of the images the wavelength associated with the fluorescence light with which the image was acquired.

In some embodiments of the above-described method and apparatus, a plurality of detectors are provided around a perimeter to survey, and the light source is used to emit light between the light source and each of the detectors to detect the absorbance as a function of the wavelength between the light source and each of the detectors.

Other objects, advantages and features of the present invention will become more apparent upon reading of the following non-restrictive description of preferred embodiments thereof, given by way of example only with reference to the accompanying drawings.

DETAILED DESCRIPTION

Figure 1:
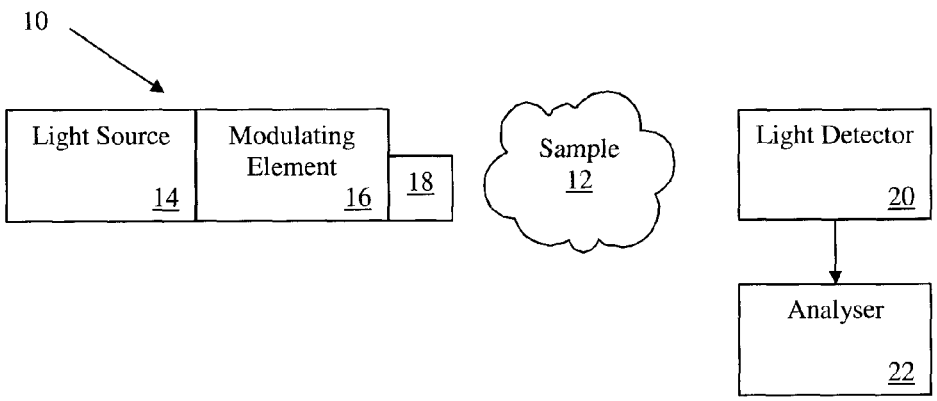
FIG. 1, in a schematic view, illustrates an apparatus for assessing an interaction of a sample with light beams having different wavelengths in accordance with an embodiment of the present invention.

With the reference to FIG. 1, there is shown an apparatus 10 for measuring the interaction of a sample 12 with light beams having different wavelengths. The apparatus 10 includes a light source 14, a modulating element 16, a light guiding element 18, a light detector 20 and an analyzer 22.

The light source 14 is provided for emitting light and includes the modulating element 16 for periodically modulating at a modulation frequency an intensity of the light emitted by the light source 14. The modulation frequency is a predetermined function of a wavelength of the light. Typically, the light source 14 is substantially monochromatic and wavelength tunable, but other types of light sources are within the scope of the present invention. For the purpose of this document, monochromatic refers to light including a relatively narrow interval of wavelengths. Examples of light sources 14 that are monochromatic include lasers, laser diodes, and LEDS, among others. Regarding the wavelength tunability of the light source 14, the light source 14 has an optical wavelength that is selectively adjustable within a predetermined bandwidth.

The light guiding element 18 is optically coupled to the light source 14 for guiding the light emitted by the light source 14 to the sample 12.

The light detector 20 is provided for receiving a response light coming from the sample 12 when the sample 12 is illuminated with the light source 14. The analyzer 22 is operatively coupled to the light detector 22 for analyzing time-varying intensity fluctuations in the response light to determine the modulation frequency.

While the apparatus 10 includes a modulating element 16 that periodically modulates the light emitted by the light source 14, in other embodiments of the invention, the light is modulated according to a non-periodic modulation function.

The light source 14 is optically coupled to the light detector 20 with the sample 12 inserted in the optical path between the light source 14 and the light detector 20. The sample 12 is any suitable sample, such as a gas, a liquid, a solid or a plasma.

The proposed apparatus 10 is a general apparatus that has many applications. For example, when the interaction between the sample 12 and the light is an absorption of the light by the sample 12, and the light detector 20 detects the intensity of the light that has not been absorbed by the sample 12, the apparatus 10 is a spectrometer. In another example, the sample 12 is a biological tissue that has been stained with fluorescent molecular probes that each emit a fluorescence light at a common wavelength in response to being irradiated with light having a wavelength that is uniquely associated with each molecular probe. Using a light detector 20 that includes a camera and suitable optical components results in an apparatus 10 that is a fluorescence microscope. Many other examples of implementation are also within the scope of the claimed invention.

While the time dependent intensity profile with which the light is modulated is, in some embodiments of the invention, arbitrary, a specific light source 14 described hereinbelow has been found to be particularly advantageous in some embodiments of the invention. This specific light source is a pulsed laser in which the wavelength emitted by the laser is dependent upon the pulse repetition rate of the laser. Therefore, the time dependent intensity profile is composed of periodic pulses having a temporal repetition rate that is dependent upon the wavelength emitted by the laser. Such a laser is described in PCT application serial number PCT/CA2008/001437 filed on Aug. 8, 2008, by Villeneuve and Godbout, the contents of which is hereby incorporated by reference in its entirety.

Briefly, this laser includes a tunable laser cavity for selectively emitting laser light having a first wavelength and a second wavelength using pump light emitted by a pump light source. The tunable laser cavity includes an optical resonator, the optical resonator having a configuration, optical properties and dimensions such that a first round-trip time of the laser light having the first wavelength in the optical resonator differs from a second round-trip time of the laser light having the second wavelength in the optical resonator. A gain medium is inserted in the optical resonator, the gain medium being responsive to the pump light for converting the pump light to the laser light. A pump light input port is optically coupled to the gain medium for receiving the pump light and conveying the pump light to the gain medium. An optical intensity modulator, acting as the modulating element 16, is inserted in the optical resonator for absorbing a portion of the laser light as the laser light propagates back and forth in the optical resonator, the optical intensity modulator having a light absorption coefficient that is modulated with a modulation period, the modulation period being selectively adjustable between a first modulation period value and a second modulation period value, the first and second round-trip times being substantially equal to a respective integer multiple of respectively the first and second modulation period values. An output port releases the laser light from the optical resonator. When the gain medium is pumped with the pump light, modulating the optical intensity modulator at the first modulation period value produces laser light having the first wavelength and modulating the optical intensity modulator at the second modulation period value produces laser light having the second wavelength. Typically, the laser is operable along a continuous spectrum between the first and second wavelengths. While this specific laser as been found advantageous in some embodiments of the invention, the reader skilled in the art will readily appreciate that any suitable light source 14 is usable in other embodiments of the invention. In many embodiments, the light source 14 is substantially continuously tunable in wavelength.

The light detector 20 may be a broad spectrum detector. In these embodiments, the light detector 20 registers the intensity of the light incoming at the light detector 20 as a function of time over a relatively broad range of optical wavelengths. In some embodiments of the invention, the detection efficiency of the light detector 20 is substantially constant over the whole wavelength range at which measurements are to be taken. However, in other embodiments of the invention, the detection efficiency is wavelength dependent and corrections based on a calibration of the light detector 20 have to be made to get a proper intensity measurement. Also, in some embodiments of the invention, the light detector 20 includes a camera for acquiring images of the sample 12.

In the embodiment of the invention in which the light source 14 is the above described pulsed laser, computing a Fourier transform of the time variable intensity profile of light measured by the light detector 20 or using a frequency counter provides the pulse repetition rate, and therefore, due to the predetermined relationship between the pulse repetition rate and the wavelength of the light emitted by the laser, provides the wavelength at which measurement is taken. This relationship can be either mathematical, formula-based, or it can be provided by a lookup table, among other possibilities.

Figure 2:
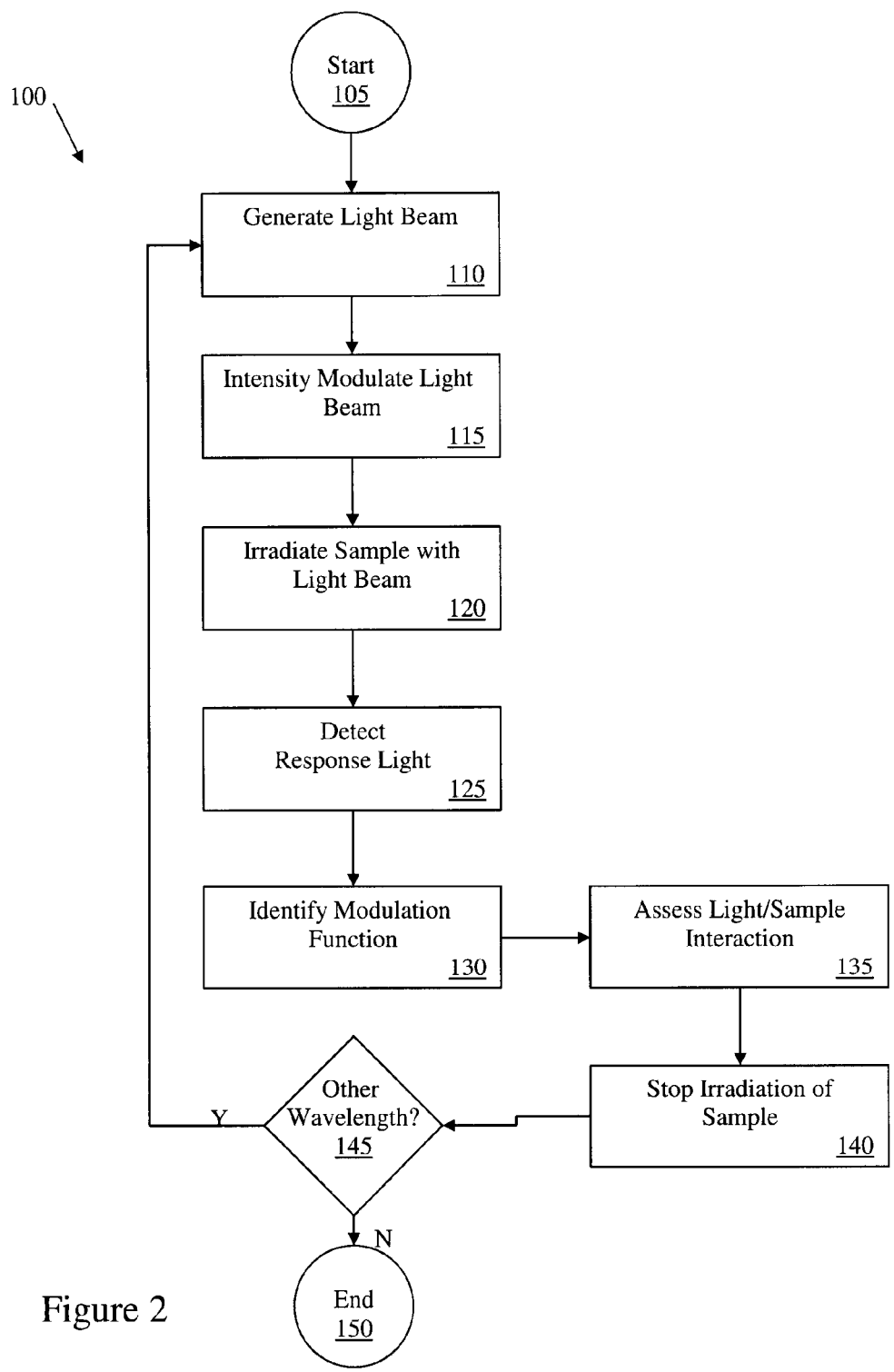
FIG. 2, in a flowchart, illustrates a method performed by the system shown in FIG. 1.

FIG. 2 illustrates a method 100 for assessing an interaction of the sample 12 with light beams having different wavelengths that can be performed by the apparatus 10. The method starts at step 105. At step 110, a light beam having a wavelength is generated by the light source 14. At step 115 the light beam is intensity modulated, using the modulating element 16, according to a modulation function that is typically unique to the wavelength of the light beam. In other words, an intensity modulation is created in the light beam. Then, at step 120, the sample 12 is irradiated with the light beam.

Subsequently, at step 125, a response light is detected from the sample 12, the response light being released by the sample 12 when the sample 12 is irradiated with the light beam. Detection is performed by the light detector 20. The response light has intensity fluctuations caused by the intensity modulation of the light beam used to irradiate the sample 12. Afterwards, at step 130, the analyzer 22, using the intensity fluctuations in the response light, identifies the modulation function and associates the wavelength and the response light to each other. The analyzer 22 also assesses the interaction of the sample with the light beam using the response light at step 135. Also, at step 140, irradiation of the sample is stopped. This step 140 can be performed either before, after, or concurrently to steps 130 and 135.

Subsequently, at step 145, a decision to either assess the interaction of the sample 12 with light at another wavelength or to stop the measurements is taken. If a new measurement is desired, the method steps back to step 110, and another measurement is taken as described herein above. Otherwise, the method ends at step 150.

The modulation functions with which the light beams of different wavelengths are modulated provide wavelength information in the light beams by encoding the wavelengths in the light beams, the wavelength information being conveyed in the response lights.

At step 115, the intensity modulation is performed in any manner allowing association of a single one of the wavelengths to each of the response lights. For example, the modulation function is substantially periodic, which has many advantages, including robustness to noise and relatively easy decoding in the response light. Examples of such periodic modulation function includes substantially sinusoidal modulation functions and pulsed modulation functions including a series of pulses. For example, each of the pulse is a gaussian pulse, a square pulse, a triangular pulse, or any other suitable pulse.

At step 120, the light is emitted for a duration sufficient for providing a good measurement of the interaction between the sample 12 and the light beam at the selected wavelength and for determining with sufficient precision the wavelength of the light emitted by the light source 14 due to the time dependent intensity profile of the light detected at the light detector 20. This duration is dependent upon many factors that can be easily determined by the reader skilled in the art using standard pattern matching and spectral analysis methods, as well as standard signal to noise ratio calculations.

By varying the wavelength of the light emitted at step 115 over a predetermined range, a spectral analysis of the sample 12 can be performed. If the above described laser is used, adding relatively slowly time dependent modulation to the intensity of the light emitted at step 115 allows for the use of conventional time of flight techniques to obtain a distance between the light source 14 and the sample 12.

At step 130, identifying the modulation function in the response light includes fitting the intensity fluctuations in the response light to a definable function. For example, a family of modulation functions is defined as a base function depending on a parameter, and finding the parameter identifies the modulation function used to modulate the light beam. In some embodiments of the invention, the modulation function is periodic and computing a Fourier transform of the intensity fluctuations in the response light provides the period of the modulation function.

In some embodiments of the invention, assessing the interaction of the sample with the first and second light beams at step 135 includes assessing a wavelength dependent spectroscopic characteristic of a sample 12, such as a an absorption or a reflection of the generated light beams by the sample 12, assessing a scattering of the generated light beams by the sample 12, assessing a non-linear interaction between the sample 12 and the beams, with or without concurrent illumination with a light beam having another wavelength, imaging a spatial distribution in the sample of emissions of the response light corresponding with each wavelength, and assessing the manner in which light at another wavelength is emitted by the sample 12 when illuminated with each wavelength, among other possibilities. Such assessments are computed using curve-fitting techniques, maximal intensity measurements, or average intensity measurements over a predetermined time period, among other possibilities.

In some embodiments of the invention, the method 100 is performed using many light beams having each a respective beam wavelength comprised between a minimal wavelength and a maximal wavelength. For example, in these embodiments, each of the modulation functions is periodic with a respective period. It is often advantageous in these embodiments to have periods that are a monotonous function of the intermediate wavelengths, or in other words, to have periods that always increase, or always decrease, as the wavelength is increased. In some examples of implementation, each of the light beams has a respective beam bandwidth and the light beams have beam wavelengths separated from each other by a wavelength differential substantially equal to the beam bandwidths.

The system of FIG. 1 is also usable in many other applications. For example, in some applications, the sample 12 is to be imaged with chromophores that attach to various locations in the sample 12. For the purpose of this document, the terminology chromophore is used to describe any substance that receives light at a first wavelength and reemits light at another wavelength and that is spatially delimited. For example, all the chromophores emit light at the same predetermined wavelength, which simplifies the light detector 20 that then needs only to be sensitive at this single wavelength. However, in other examples, light is emitted by the chromophores at different wavelengths.

By using the light source 14, the identity of each chromophore is encoded in the intensity fluctuations of light emitted by the chromophore, as these intensity fluctuations are encoded by the nature of the light source 14 and each chromophore reacts to only one wavelength. To allow imaging, in some embodiments of the invention, the light detector 20 includes an image detector, such as a camera. In these embodiments, to facilitate identification of the wavelength of the light incoming at the sample 12, it may be useful to direct a portion of the emitted light to a time-dependent intensity profile analyzer to associate with each image recorded a wavelength of light emitted by the light source 14.

In other words, the wavelength of light incoming at each choromophore is encoded in a time-varying intensity profile of this light; for example, a frequency of a periodic variation, which allows using many chromophores having different excitation wavelengths, but a single emission wavelength, without synchronizing the light source 14 and the light detector 20 as the frequency of variation in light intensity corresponds to a specific excitation wavelength. Also, this embodiment allows for the use of a light detector 20 that does not include a spectrometer as emission wavelength discrimination is no longer required if all the chromophores emit at the same wavelength due to the encoding of excitation wavelength with periodic intensity variations.

Figure 4:
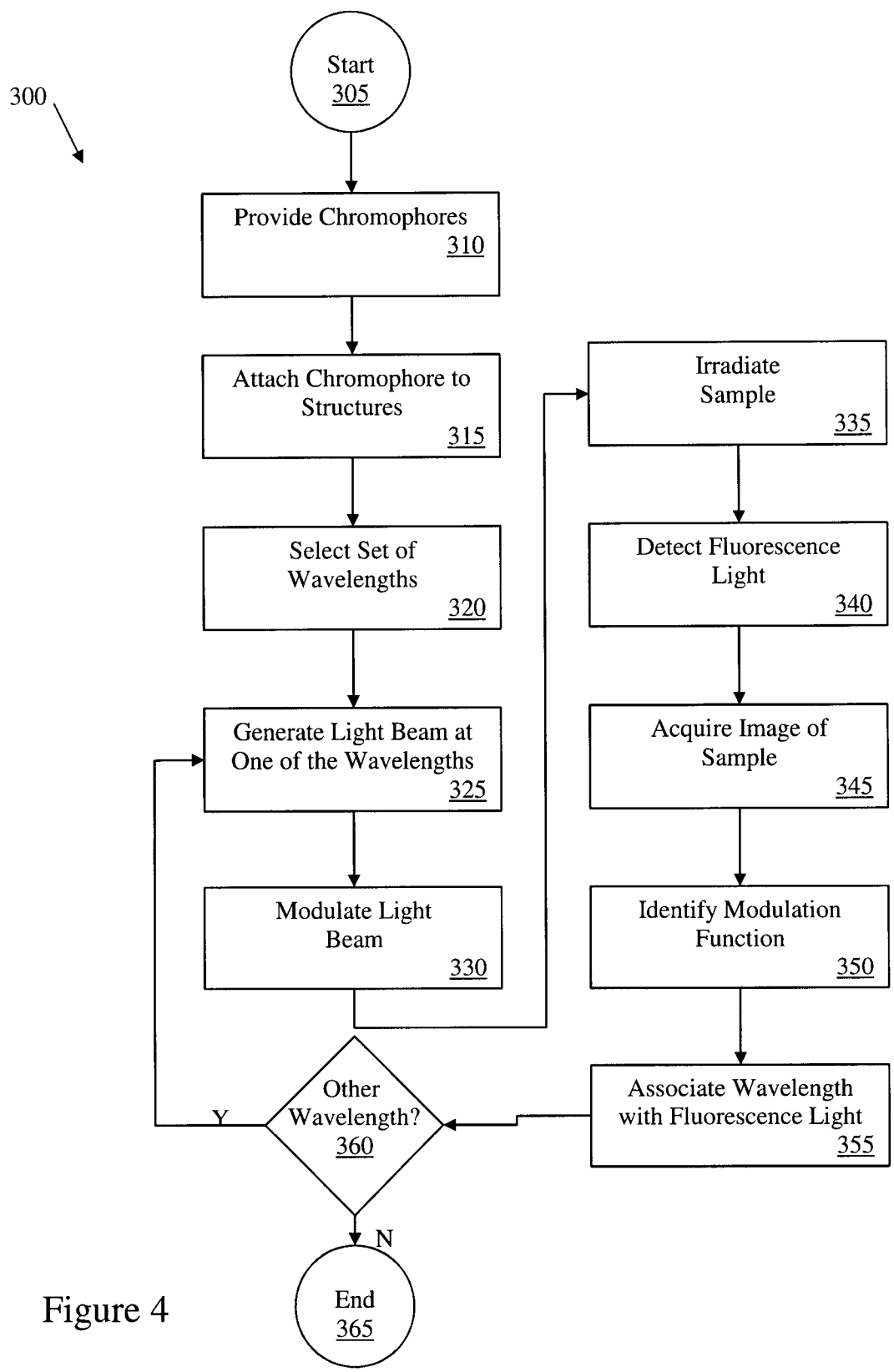
FIG. 4, in a flowchart, illustrates another method performed by the system shown in FIG. 1.

FIG. 4 illustrates a method 300 for imaging a distribution of predetermined structures in a biological sample using fluorescent chromophores. The method starts at step 305. At step 310, at least two chromophores are provided, each of the chromophores emitting fluorescence light at a common predetermined wavelength when irradiated with light having different irradiation wavelengths. Each of the chromophores is attachable to a different one of the predetermined structures. Afterwards, at step 315, the chromophores are attached to the predetermined structures. Chromophores and their methods of use are well-known in the art and will therefore not be described in further details herein.

Afterwards, a loop is made to irradiate the biological sample 12 with light beams having wavelengths causing fluorescence in the chromophores. To that effect, at step 320, a set of wavelengths is selected to correspond to the excitation wavelengths of the chromophores. Then, at step 325, one of the wavelengths from the set of wavelengths is selected and a light beam having this wavelength is generated. At step 330, the light beam is intensity modulated in time according to a respective modulation function associated with the wavelength. At step 335, the biological sample 12 is irradiated with the light beam and, at step 340, the fluorescence light emitted by the chromophores in the biological sample 12 at the common predetermined wavelength in response to irradiation with the light beam is detected.

Subsequently, at step 345, an image of the biological sample is acquired when the biological sample emits the fluorescence light. Also, at step 350, a modulation function is identified in each of the fluorescence lights using time-varying intensity fluctuations in each of the fluorescence lights and, at step 355, one of the wavelengths is associated to the fluorescence lights, the wavelength associated with the fluorescence lights being the wavelength associated with the modulation function identified in the fluorescence light, which is the wavelength of the light used to irradiate the biological sample 12 at step 335. Finally, if not all wavelengths were used, at step 360, the method loops back to step 325. Otherwise, the method ends at step 365. The steps contained within the loop of the method 300 are substantially similar to similar steps described hereinabove with respect to the method 100 and are therefore not described in further details.

Figure 3:
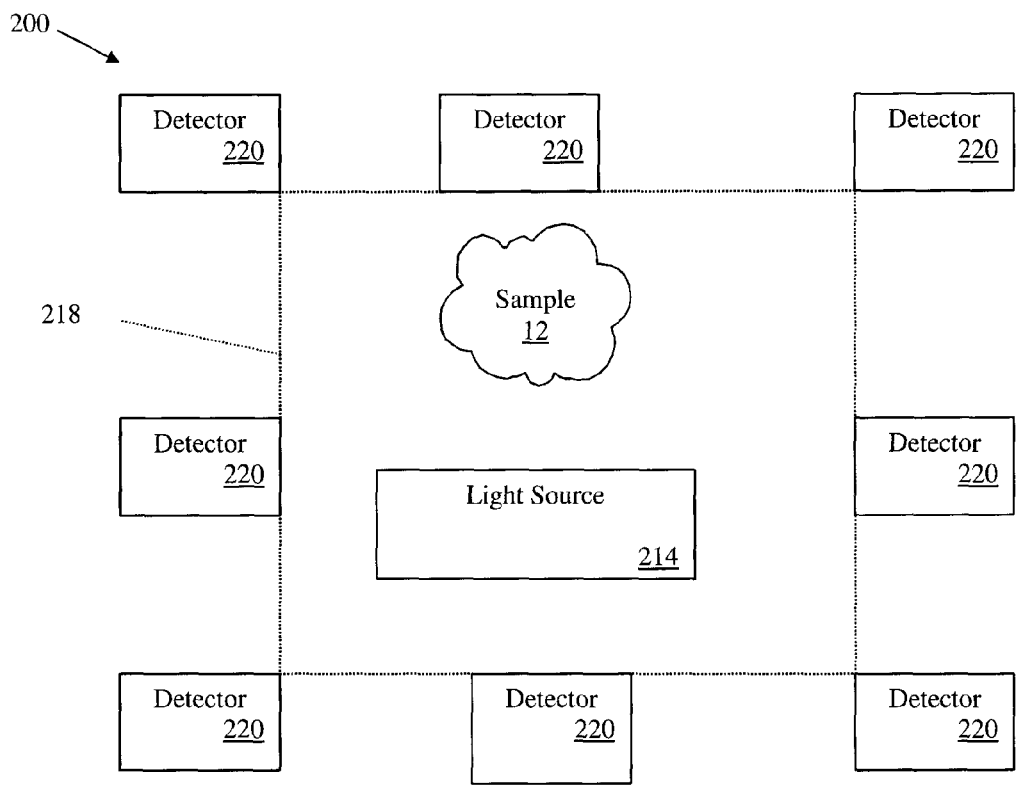
FIG. 3, in a schematic view, illustrates an apparatus for measuring the interaction of a sample with light beams having different wavelengths in accordance with another embodiment of the present invention.

FIG. 3 illustrates an alternative system 200 in which the method 100 is used to survey the fluid contents of a perimeter 218. To that effect, a light source 214, substantially similar to the light source 14, is provided inside the perimeter 218. A plurality of light detectors 220, each similar to the light detector 20, are provided around the perimeter 218. The light detectors 220 may be fixed, or they may be mobile by being mounted to vehicles, humans, or animals, among other possibilities. The light source 214 is able to emit light towards all the light detectors 220. To that effect, the light source 214 may be mounted onto a variable orientation device, or a fixed light emitting element can be used and mirrors can be used to redirect the light emitted by a fixed light source towards the light detectors 220. In yet other embodiments of the invention, a plurality of light sources 214 are used, each of these light sources being optically coupled with one of the light detectors 220.

The above described system 200 is usable in many situations, including, non-limitingly, for the surveillance of gaseous emissions from a factory, and for soldier protection by detecting the presence of harmful substances in a sample 12 of air in the perimeter 218.

Although the present invention has been described hereinabove by way of preferred embodiments thereof, it can be modified without departing from the spirit and nature of the subject invention as defined in the appended claims.

What is claimed is:

1. A method for assessing an interaction of a sample with light beams having different wavelengths from a first wavelength to a second wavelength, said method comprising:
generating a first light beam having said first wavelength, said first light beam being intensity modulated according to a first modulation function to create a first intensity modulation in said first light beam;
irradiating said sample with said first light beam;
detecting a first response light from said sample, said first response light being released by said sample when said sample is irradiated with said first light beam, said first response light having first intensity fluctuations caused by said first intensity modulation;
using said first intensity fluctuations in said first response light to identify said first modulation function and associate said first wavelength and said first response light to each other;
assessing said interaction of said sample with said first light beam using said first response light;
stopping irradiating said sample with said first light beam;
generating a plurality of intermediate light beams each having a respective intermediate beam wavelength comprised between said first and second wavelengths, each of said intermediate light beams being intensity modulated according to a respective intermediate modulation function to create a respective intermediate intensity modulation in each of said intermediate light beams;
successively irradiating said sample with each of said intermediate light beams;
detecting intermediate response lights from said sample, said intermediate response lights being each released by said sample when said sample is irradiated with a respective one of said intermediate light beams, said respective intermediate intensity modulations causing each respective intermediate intensity fluctuations in said respective intermediate response light;
using said intermediate intensity fluctuations in said intermediate response lights to identify said intermediate modulation functions and associate a respective one of said intermediate wavelengths and a respective one of said intermediate response lights to each other;
assessing said interaction of said sample with said intermediate light beams using said intermediate response lights;
generating a second light beam having said second wavelength, said second light beam being intensity modulated according to a second modulation function to create a second intensity modulation in said second light beam;
irradiating said sample with said second light beam after stopping irradiating said sample with said first light beam and said intermediate light beams;
detecting a second response light from said sample, said second response light being released by said sample when said sample is irradiated with said second light beam, said second response light having second intensity fluctuations caused by said second intensity modulation;
using said second intensity fluctuations in said second response light to identify said second modulation function and associate said second wavelength and said second response light to each other;
assessing said interaction of said sample with said second light beam using said second response light;
whereby said first, intermediate and second modulation functions provide wavelength information in said first, intermediate and second light beams by encoding said first, intermediate beam and second wavelengths in said first, intermediate and second light beams, said wavelength information being conveyed in said first, intermediate and second response lights to allow association of said first, intermediate and second response lights respectively with said first, intermediate beam and second wavelengths.

2. A method as defined in claim 1, wherein assessing said interaction of said sample with said first and second light beams includes assessing an absorption of said first and second light beams by said sample.

3. A method as defined in claim 1, wherein assessing said interaction of said sample with said first and second light beams includes assessing a reflection of said first and second light beams by said sample.

4. A method as defined in claim 1, wherein assessing said interaction of said sample with said first and second light beams includes assessing scattering of said first and second light beams by said sample.

5. A method as defined in claim 1, wherein assessing said interaction of said sample with said first and second light beams includes assessing a non-linear interaction between said sample and said first and second light beams.

6. A method as defined in claim 1, wherein assessing said interaction of said sample with said first and second light beams includes imaging a spatial distribution of emission in said sample of said first and second response lights.

7. A method as defined in claim 1, wherein said first response light is emitted by said sample at a third wavelength, said third wavelength differing from said first wavelength.

8. A method as defined in claim 1, wherein said first modulation function is substantially periodic.

9. A method as defined in claim 8, wherein said first modulation function is substantially sinusoidal.

10. A method as defined in claim 8, wherein said first modulation function includes a series of pulses.

11. A method as defined in claim 1, wherein said first and second modulation functions define respectively a first phase and a second phase, said first and second phases being associated respectively with said first and second wavelengths.

12. A method as defined in claim 1, wherein said intermediate modulation functions are each periodic with a respective period.

13. A method as defined in claim 12, wherein for all said intermediate light beams, said periods are a monotonous function of said intermediate beam wavelengths.

14. A method as defined in claim 1, wherein each of said intermediate light beams has a respective intermediate beam bandwidth, said intermediate light beams having intermediate beam wavelengths separated from each other by a wavelength differential substantially equal to said intermediate beam bandwidths.

15. A method as defined in claim 1, wherein identifying said first modulation function in said first response light includes fitting said intensity fluctuations in said first response light to a definable function.

16. A method as defined in claim 1, wherein identifying said first modulation function in said first response light includes computing a Fourier transform of said intensity fluctuations in said first response lights.

17. A method as defined in claim 1, wherein generating said first light beam includes generating said first light beam with a laser light source.

18. A method as defined in claim 1, wherein generating said first and second light beams includes generating said first and second light beams with a common laser light source.

19. A method as defined in claim 18, wherein said common laser light source includes a wavelength tunable laser.

20. A method as defined in claim 19, wherein said common laser light source is substantially continuously tunable in wavelength between said first and second wavelengths.

21. A method as defined in claim 1, further comprising acquiring an image of said sample with said first response light.

* * * * *